United States Patent
Chern et al.

(10) Patent No.: US 6,946,470 B2
(45) Date of Patent: Sep. 20, 2005

(54) METHOD OF TREATING PSYCHOSIS IN A PATIENT

(75) Inventors: Ji-Wang Chern, Taipei (TW); Feng-Nien Ko, Taipei (TW)

(73) Assignees: Medical and Pharmaceutical Industry Technology and Development Center, Taipei Hsien (TW); National Science Council, Taipei (TW)

( * ) Notice: Subject to any disclaimer, the term of this patent is extended or adjusted under 35 U.S.C. 154(b) by 90 days.

(21) Appl. No.: 10/704,801

(22) Filed: Nov. 12, 2003

(65) Prior Publication Data

US 2005/0049266 A1 Mar. 3, 2005

Related U.S. Application Data

(62) Division of application No. 10/142,880, filed on May 13, 2002, now abandoned.

(30) Foreign Application Priority Data

Jan. 4, 2002 (TW) .................................... 91100075 A

(51) Int. Cl.$^7$ ................ A61P 25/18; A61K 31/519; C07D 487/04
(52) U.S. Cl. ................................................. 514/267
(58) Field of Search ........................... 514/267; 544/250

(56) References Cited

U.S. PATENT DOCUMENTS

| | | | |
|---|---|---|---|
| 5,158,953 A | 10/1992 | Chern et al. | 514/267 |
| 5,340,814 A | 8/1994 | Chern et al. | 514/267 |
| 5,512,677 A | 4/1996 | Chern et al. | 544/250 |
| 5,932,584 A | 8/1999 | Chern et al. | 514/267 |

*Primary Examiner*—Thomas C. McKenzie
(74) *Attorney, Agent, or Firm*—Bacon & Thomas

(57) ABSTRACT

A method of treating psychosis in a patient which comprises administering a pharmaceutical composition useful in treating psychosis containing a therapeutically effective amount of 1-[piperidinyl]methyl-2,3-dihydroimidazo[1,2-c]quinazolin-5(6H)-one as an active ingredient.

8 Claims, No Drawings

METHOD OF TREATING PSYCHOSIS IN A PATIENT

This application is a divisional application of abandoned U.S. application Ser. No. 10/142,880, filed May 13, 2002 (of which the entire disclosure of the pending, prior application is hereby incorporated by reference).

FIELD OF THE INVENTION

The invention of the present application is related to a method of using 2-[piperidinyl]methyl-2,3-dihydroimidazo [1,2-c]quinazolin-5(6H)-one in treating psychosis in a patient.

BACKGROUND OF THE INVENTION

U.S. Pat. No. 5,158,953 discloses synthesis of a novel series of 2-substituted methyl-2,3-dihydroimidazo[1,2-c] quinazolin-5(6H)-ones (-thiones) compounds, and they are found useful as an active ingredient for the prophylaxis and treatment of hypertension.

U.S. Pat. No. 5,340,814 and U.S. Pat. No. 5,512,677 disclose a novel series of 3-substituted methyl-2,3-dihydroimidazo[1,2-c]quinazoline-5(6H)-ones (-thiones) compounds. These compounds are found useful as an active ingredient for the treatment of hypertension and dysuria.

U.S. Pat. No. 5,932,584 discloses novel optically active 3-substituted methyl-5-methylthio-2,3-dihydroimidazo[1,2-c]quinazoline (I) and 3-substituted methyl-2,3-dihydroimidazo[1,2-c]quinazolin-5(6H)-one (II). These compounds are found useful as an active ingredient for the treatment of hypertension and dysuria.

Heretofore, the series of 2-substituted or 3-substituted methyl-2,3-dihydroimidazo[1,2-c]quinazolin-5(6H)-ones (-thiones) compounds have not been found other pharmaceutical activity in addition to as an active ingredient for the treatment of hypertension and dysuria.

SUMMARY OF THE INVENTION

A primary objective of the present invention is to provide a new use of 2-[piperidinyl]methyl-2,3-dihydroimidazo[1,2-c]quinazolin-5(6H)-one in treating psychosis in a patient.

An antipsychotic pharmaceutical composition provided according to the present invention comprises an antipsychosis therapeutically effective amount of 2-[piperidinyl] methyl-2,3-dihydroimidazo[1,2-c]quinazolin-5(6H)-one having the following formula or a pharmaceutically acceptable salt thereof, as an active ingredient, in combination with a pharmaceutically acceptable carrier or diluent for the active ingredient:

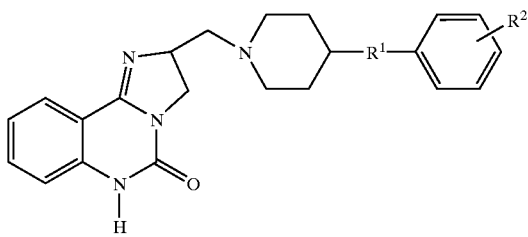

wherein $R^1$ is C1–C6 alkylene, carbonyl, C1–C6 alkylene carbonyl or carbonyloxy; and $R^2$ is hydrogen, C1–C6 alkyl, C1–C6 alkoxy or halogen.

Preferably, $R^1$ is methylene or carbonyl, and more preferably is carbonyl.

Preferably, $R^2$ is hydrogen or halogen, more preferably is halogen, and most preferably is fluorine.

Preferably, the antipsychotic pharmaceutical composition of the present invention is administered orally.

DETAILED DESCRIPTION OF THE INVENTION

2-[Piperidinyl]methyl-2,3-dihydroimidazo[1,2-c] quinazolin-5(6H)-ones were synthesized according to the method disclosed in U.S. Pat. No. 5,158,953, the details of which are incorporated herein by reference. Dopamine $D_{2L}$ receptor binding assay and serotonin 5-HT$_2$ receptor binding assay were conducted to evaluate these compounds as potential antipsychotic $D_{2L}$/5-HT$_2$ antagonists. It is believed that a significantly greater affinity for the 5-HT$_2$ receptor than for the $D_{2L}$ receptor has the best possibility of exhibiting an atypical profile.

Two compounds having $D_{2L}$/5-HT$_2$ affinity ratios less than 1 were evaluated as to their potential antipsychotic activities by testing their effects on apomorphine-induced climbing behavior in mice. Inhibition of climbing would suggest that a compound was a $D_{2L}$ antagonist, a characteristic of all clinically effective antipsychotics.

Dopamine $D_{2L}$ Receptor Binding Assay

This assay measures binding of [$^3$H]Spiperone to human dopamine $D_{2L}$ receptors. CHO cells stably transfected with a plasmid encoding the human dopamine $D_{2L}$ receptor were used to prepare membranes in modified Tris-HCl pH 7.4 buffer. A 20 μg aliquot of membrane, in the presence or absence of a test compound, was incubated with 0.16 nM [$^3$H]Spiperone for 120 minutes at 25° C. Non-specific binding was estimated in the presence of 10 μM hapoperidol. Membranes were filtered and washed three times and the filters were counted to determine [$^3$H]Spiperone specifically bound. [References: Grandy D K, Marchionni M A, Makam H, Stofko R E, Alfano M, Frothingham L, Fischer J B, Burker-Howie K J, Bunzow J R, Server A C. Proc. Natl. Acad. Sci. (USA) 86: 9762–9766, 1989; Bunzow J R, Van Tol H H, Grandy D K, Albert P, Salon J, Christie M, Machida C A, Neve K A, Civelli O. Nature 336: 783–787, 1988; Hayes G, Biden T J, Selbie L A, Shine J. Mol. Endocrin. 6: 920–926, 1992]

Serotonin 5-HT$_2$ Receptor Binding Assay

This assay measures binding of [$^3$H]Ketanserin to serotonin 5-HT$_2$ receptors. Whole brain (except cerebellum) membranes of male Wistar derived rats weighing 175±25 g were prepared in Tris-HCl pH 7.7 buffer. A 10 mg aliquot of membrane was incubated with 0.5 nM [$^3$H]Ketanserin for 40 minutes at 25° C. Non-specific binding was estimated in the presence of 1 μM Ketanserin. Membranes were filtered and washed three times and the filters were counted to determine [$^3$H]Ketanserin specifically bound. [Reference: Leysen J E, Niemegeers C J, Van Nauten J M, Laduron D M. Mol. Pharmacol. 21: 301–314, 1982]

TABLE 1

Effect of 2-[piperidinyl]methyl-2,3-dihydroimidazo[1,2-c]quinazolin-5(6H)-one compounds on radioligand binding assay

| Samples* | Concentration | Inhibition % $D_{2L}$ | 5-HT$_2$ |
|---|---|---|---|
| PDC-121 | 30 nM | 18 | 21 |
| PDC-122 | 30 nM | 13 | 2 |
| PDC-123 | 30 nM | 11 | 4 |

TABLE 1-continued

Effect of 2-[piperidinyl]methyl-2,3-dihydroimidazo[1,2-c]quinazolin-5(6H)-one compounds on radioligand binding assay

| Samples* | Concentration | Inhibition % | |
|---|---|---|---|
| | | $D_{2L}$ | $5\text{-}HT_2$ |
| PDC-124 | 30 nM | 14 | 62 |
| PDC-125 | 30 nM | 23 | 0 |
| PDC-126 | 30 nM | 29 | 11 |
| PDC-127 | 30 nM | 11 | 20 |
| PDC-130 | 30 nM | 16 | 88 |
| PDC-131 | 30 nM | 10 | 47 |
| PDC-132 | 30 nM | 15 | 5 |

*PDC-121 (Example 8 in U.S. Pat. No. 5,158,953)
2-[4-benzyl-1-piperazinyl]methyl-2,3-dihydroimidazo[1,2-c]quinazolin-5(6H)-one
PDC-122 (Example 5 in U.S. Pat. No. 5,158,953)
3-{2,3-dihydroimidazo[1,2-c]quinazolin-5(6H)-one-2-yl}methyl-azaspiro-[5,5]undecane
PDC-123 (Example 6 in U.S. Pat. No. 5,158,953)
2-[4-piperonyl-1-piperazinyl]methyl-2,3-dihydroimidazo[1,2-c]-quinazolin-5(6H)-one
PDC-124 (Example 9 in U.S. Pat. No. 5,158,953)
2-[4-Benzyl-1-piperidinyl]methyl-2,3-dihydroimidazo[1,2-c]quinazolin-5(6H)-one
PDC-126 (Example 12 in U.S. Pat. No. 5,158,953)
2-[1-benzylpiperidin-4-yl]aminomethyl-2,3-dihydroimidazo[1,2-c]-quinazolin-5(6H)-one
PDC-127 (Example 11 in U.S. Pat. No. 5,158,953)
2-[4-(4-fluorobenzyl)-1-piperazinyl]methyl-2,3-dihydroimidazo[1,2-c]quinazolin-5(6H)-one
PDC-130 (Example 15 in U.S. Pat. No. 5,158,953)
2-[1-(4-p-fluorobenzoyl)piperidinyl]methyl-2,3-dihydroimidazo[1,2-c]-quinazolin-5(6H)-one
PDC-131 (Example 14 in U.S. Pat. No. 5,158,953)
2-[1-(4-chlorobenzhydryl)piperazinyl]methyl-2,3-dihydroimidazo[1,2-c]-quinazolin-5(6H)-one
PDC-132 (Example 16 in U.S. Pat. No. 5,158,953)
2-[1-(4-methoxyphenyl)piperazinyl]methyl-2,3-dihydroimidazo[1,2-c]-quinazolin-5(6H)-one Effects on Apomorphine-Induced Climbing Behavior Test substance was administered PO (30 mg/kg, initial dose) to a group of 3 ICR derived male or female mice preselected non-climbing animals weighing 22±2 gms placed in specially constructed cages. Climbing behavior was scored 0–2 for each animal from 30 to 60-minutes post-dosing: all four paws on floor=0, both forefeet holding the wall=1, all four paws on wall=2. Consequently, maximum possible group score was 2×3 mice=6. A score of 3 or more (≧3) during this 30 minute observation period denotes dopamine-agonist activity. Mice in which no significant dopamine agonist activity occurred were then used to determine antagonistic activity. Sixty minutes after administration of test substance PO (30 mg/kg), apomorphine (1 mg/kg, SC) was administered and the climbing behavior was observed and scored during the 30 minutes. In groups of three vehicles treated animals, this dose of apomorphine consistently induced climbing behavior with scores of 5–6 recorded. [Reference: Psychopharmacology 50: 1–6, 1976] Percentage inhibition of test substance on apomorphine-induced climbing behavior is calculated as follows:

$$\text{Inhibition \%} = \frac{[(\text{Scores of apomorphine group}) - (\text{Scores of test substance group})]}{(\text{Scores of apomorphine group})} \times 100\%$$

TABLE 2

Effect on apomorphine-induced climbing behavior

| Sample* | Route | dose | Agonist activity (score) | Inhibition % |
|---|---|---|---|---|
| Vehicle (2% Tween 80) | PO | 20 ml/kg | 0 | 0 |
| PDC-124 | PO | 30 mg/kg | 0 | 50 |
| PDC-130 | PO | 30 mg/kg | 0 | 100 |
| PDG-130 | PO | 10 mg/kg | 0 | 100 |
| PDC-130 | PO | 3 mg/kg | 0 | 60 |
| PDC-130 | PO | 1 mg/kg | 0 | 0 |

*PDC-124 and PDC-130 are defined the same as in Table 1

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of treating psychosis in a patient comprising administering to the patient an antipsychosis therapeutically effective amount of 2-[piperidinyl]methyl-2,3-dihydroimidazo[1,2-c]quinazolin-5(6H)-one having the following formula or a pharmaceutically acceptable salt thereof:

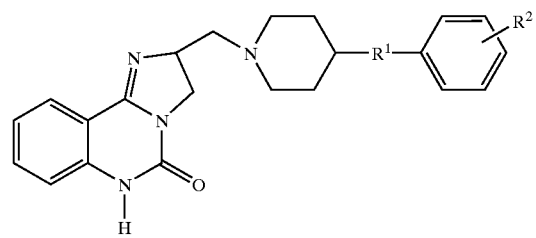

wherein $R^1$ is C1–C6 alkylene, carbonyl, C1–C6 alkylene carbonyl or carbonyloxy; and $R^2$ is hydrogen, C1–C6 alkyl, C1–C6 alkoxy or halogen.

2. The method according to claim 1, wherein $R^1$ is methylene or carbonyl.

3. The method according to claim 2, wherein $R^1$ is carbonyl.

4. The method according to claim 1, wherein $R^2$ is hydrogen or halogen.

5. The method according to claim 2, wherein $R^2$ is hydrogen or halogen.

6. The method according to claim 3, wherein $R^2$ is halogen.

7. The method according to claim 6, wherein $R^2$ is fluorine.

8. The method according to claim 6, wherein said 2-[piperidinyl]methyl-2,3-dihydroimidazo[1,2-c]quinazolin-5(6H)-one or a pharmaceutically acceptable salt thereof is orally administered.

* * * * *